United States Patent
Wiant et al.

(10) Patent No.: US 12,406,759 B2
(45) Date of Patent: Sep. 2, 2025

(54) FITNESS SCORE USING HEART RATE RECOVERY DATA

(71) Applicant: Myx Fitness, LLC, El Segundo, CA (US)

(72) Inventors: Matthew Wiant, Fairfield, CT (US); Mohammed Iqbal, Arlington, VA (US)

(73) Assignee: MYX Fitness, LLC, El Segundo, CA (US)

(*) Notice: Subject to any disclaimer, the term of this patent is extended or adjusted under 35 U.S.C. 154(b) by 901 days.

(21) Appl. No.: 17/595,995

(22) PCT Filed: Apr. 10, 2020

(86) PCT No.: PCT/US2020/027738
§ 371 (c)(1),
(2) Date: Dec. 1, 2021

(87) PCT Pub. No.: WO2020/256814
PCT Pub. Date: Dec. 24, 2020

(65) Prior Publication Data
US 2022/0399097 A1      Dec. 15, 2022

Related U.S. Application Data

(60) Provisional application No. 62/864,849, filed on Jun. 21, 2019.

(51) Int. Cl.
*G16H 20/30* (2018.01)
*A63B 24/00* (2006.01)

(52) U.S. Cl.
CPC ......... *G16H 20/30* (2018.01); *A63B 24/0062* (2013.01); *A63B 24/0075* (2013.01); *A63B 2024/0065* (2013.01)

(58) Field of Classification Search
CPC .... G16H 20/30; G16H 50/30; A63B 24/0062; A63B 24/0075; A63B 2024/0065
See application file for complete search history.

(56) References Cited

U.S. PATENT DOCUMENTS

| 5,692,501 A | 12/1997 | Minturn |
| 9,149,195 B2 | 10/2015 | Hadley |
| (Continued) | | |

FOREIGN PATENT DOCUMENTS

| CN | 109646876 A | 4/2019 |
| WO | 2020256814 A1 | 12/2020 |

OTHER PUBLICATIONS

Yeh et al, The Reliability and Validity of a Modified Squat Test to Predict Cardiopulmonary Fitness in Healthy Older Men. BioMed Research International, vol. 2018, Jan. 2, 2018 [retrieved on Dec. 19, 2024]. From Internet <URL: https://pmc.ncbi.nlm.nih.gov/articles/PMC5816896/pdf/BMRI2018-4863454.pdf> (Year: 2018).*

(Continued)

*Primary Examiner* — Gary Jackson
*Assistant Examiner* — Sebastian X Lukjan
(74) *Attorney, Agent, or Firm* — Hamilton, Brook, Smith & Reynolds, P.C.

(57) ABSTRACT

Embodiments provide functionality for determining fitness level of an individual using a fitness testing unit. In one such embodiment, an individual is instructed, via a graphical user interface (GUI) of a fitness testing unit, to perform a series of exercise activities. In turn, via the fitness testing unit, baseline heart rate, maximum heart rate, and recovery heart rate are captured while the individual is performing the series of exercise activities. Then, a fitness level of the individual is determined using an age of the individual and the captured baseline heart rate, maximum heart rate, and recovery heart rate.

20 Claims, 5 Drawing Sheets

(56) References Cited

U.S. PATENT DOCUMENTS

| | | |
|---|---|---|
| 2007/0232454 A1 | 10/2007 | Kagan et al. |
| 2007/0249949 A1 | 10/2007 | Hadley |
| 2011/0040193 A1 | 2/2011 | Seppanen et al. |
| 2013/0123071 A1* | 5/2013 | Rhea ............... A63B 24/00 482/8 |
| 2014/0088444 A1 | 3/2014 | Saalasti et al. |
| 2014/0323880 A1 | 10/2014 | Ahmed et al. |
| 2016/0081627 A1 | 3/2016 | Mcgloin et al. |
| 2016/0278700 A1 | 9/2016 | Lee et al. |
| 2016/0302677 A1* | 10/2016 | He ............... A61B 5/1102 |
| 2016/0365006 A1* | 12/2016 | Minturn ............... G16H 15/00 |
| 2017/0027507 A1 | 2/2017 | Yeh et al. |
| 2017/0100637 A1 | 4/2017 | Princen et al. |
| 2018/0318647 A1 | 11/2018 | Foley et al. |
| 2019/0029586 A1 | 1/2019 | Saalasti et al. |
| 2019/0111318 A1 | 4/2019 | Evancha et al. |
| 2019/0143194 A1 | 5/2019 | Evancha et al. |

OTHER PUBLICATIONS

International Search Report and Written Opinion of PCT/US2020/027738 dated Jun. 29, 2020 titled "Fitness Score Using Heart Rate Recovery Data".

YMCA Bench Step Test for Cardiovascular Fitness; Feb. 29, 2019 Internet download available at: https://thehubedu-production.s3.amazonaws.com/uploads/3/fd00fae8-7453-45bf-96bb-705135c0ba27/YMCA_Bench_Step_Test_for_Cardiovascular_Fitness.pdf.

International Preliminary Report on Patentability for PCT/US2020/027738 dated Dec. 30, 2021, titled "Fitness Score Using Heart Rate Recovery Data".

Dimkpa, U., et al., "Assessment of the influence of age on the rate of heart rate decline after maximal exercise in non-athletic adult males", Clinical Physiology And Functional Imaging, vol. 29, No. 1, Nov. 2008, pp. 68-73.

Nicole Maue, "MI-Fitness test", available online at: <https://www.myzone.org/blog/users/mz-fitness-test-2>, Jan. 15, 2021, 8 pages.

\* cited by examiner

FITNESS SCORE USING HEART RATE RECOVERY DATA

RELATED APPLICATIONS

This application is the U.S. National Stage of International Application No. PCT/US2020/027738, filed on Apr. 10, 2020, published in English, which claims the benefit of U.S. Provisional Application No. 62/864,849, filed Jun. 21, 2019. The entire teachings of the above applications are incorporated herein by reference.

BACKGROUND

Fitness and, in particular, fitness instruction and tracking, have become increasingly prevalent. However, improved methods and systems for fitness instruction and tracking are needed.

SUMMARY

Embodiments provide improved fitness instruction and tracking through determination and use of a fitness score that is easy to understand and that facilitates tracking comparable fitness levels over long periods of time.

An example embodiment determines a fitness level of an individual using a fitness testing unit. Such an embodiment, first, instructs an individual, via a graphical user interface (GUI) of the fitness testing unit, to perform a series of exercise activities. Next, via the fitness testing unit, a baseline heart rate, a maximum heart rate, and a recovery heart rate of the individual are captured while the individual is performing the series of instructed exercise activities. In turn, a fitness level of the individual is determined using an age of the individual and the captured baseline heart rate, maximum heart rate, and recovery heart rate.

According to an embodiment, the series of exercise activities includes exercises of varying intensity. In one such embodiment, the series of exercise activities includes: a relaxation activity, a cardiovascular activity, and a recovery activity. In an embodiment, the baseline heart rate is captured while the individual is performing the relaxation activity, the maximum heart rate is captured while the individual is performing the cardiovascular activity, and the recovery heart rate is captured while the individual is performing the recovery activity. According to an embodiment, capturing the individual's heart rate includes continuously monitoring heart rate of the individual. Further, according to yet another embodiment, instructing the individual to perform the series of activities includes instructing the individual, via the GUI, to perform the cardiovascular activity until it is determined that the monitored heart rate of the individual is at 80% of a recommended heart rate, wherein the recommended heart rate is based on the age of the individual.

According to yet another embodiment, determining a fitness level of the individual using an age of the individual employs a factor indicating highest potential heart rate recovery given the age of the individual. Another embodiment includes obtaining the age of the individual by accessing a database storing a user profile associated with the individual. In this way, the age of the individual can be used in determining the fitness level of the individual.

In embodiments, the fitness testing unit may be any such device capable of instructing an individual to perform exercise activities and capture heart rate of the individual. For example, the fitness testing unit may be implemented using a computing device including, memory, one or more processors, and one or more communication interfaces capable of performing the functionality described herein. Further, in an embodiment, the fitness testing unit comprises a bicycle or a treadmill.

Another embodiment is directed to a fitness testing system that determines the fitness level of an individual. The system includes a processor and a memory with computer code instructions stored thereon that cause the fitness system to determine the fitness level of the individual. In an example embodiment, the system is configured to instruct an individual, via a GUI of the fitness testing system, to perform a series of exercise activities. While the individual is performing the series of exercise activities, the system captures a baseline heart rate, a maximum heart rate, and a recovery heart rate of the individual. Using the captured baseline heart rate, maximum heart rate, recovery heart rate, and an age of the individual, the system determines a fitness level of the individual.

In an embodiment of the system, the series of exercise activities includes exercises of varying intensity. For instance, in an example embodiment, the series of exercise activities includes: a relaxation activity, a cardiovascular activity, and a recovery activity. In one such example embodiment of the system, in capturing the baseline heart rate, the maximum heart rate, and the recovery heart rate, the processor and the memory, with the computer code instructions, are configured to cause the fitness testing system to capture the baseline heart rate while the individual is performing the relaxation activity, capture the maximum heart rate while the individual is performing the cardiovascular activity, and capture the recovery heart rate while the individual is performing the recovery activity.

Another embodiment of the system is configured to continuously monitor heart rate of the individual and instruct the individual, via the GUI, to perform the cardiovascular activity until it is determined that the monitored heart rate is at 80% of a recommended heart rate, wherein the recommended heart rate is based on the age of the individual. An embodiment of the system is configured to determine the fitness level of the individual using an age of the individual by employing a factor indicating highest potential heart rate recovery given the age of the individual. Yet another embodiment of the system is configured to obtain the age of the individual by accessing a database storing a user profile associated with the individual. Another example embodiment of the system is integrated into a bicycle or treadmill.

An embodiment is directed to a computer program product for determining fitness level of an individual using a fitness testing unit. The computer program product comprises one or more non-transitory computer-readable storage devices and program instructions stored on at least one of the one or more storage devices. The program instructions, when loaded and executed by a processor associated with the fitness testing unit, cause the fitness unit to determine a fitness level of an individual as described herein. For instance, in an embodiment, the program instructions cause the fitness testing unit to instruct an individual, via a GUI of the fitness testing unit, to perform a series of exercise activities. Further, in such an embodiment, the program instructions cause the fitness testing unit to (1) capture a baseline heart rate, a maximum heart rate, and a recovery heart rate of the individual while the individual is performing the series of exercise activities and (2) determine a fitness level of the individual using an age of the individual and the captured heart rates.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The teachings of all patents, published applications, and references cited herein are incorporated by reference in their entirety.

Cardiac health, measured by the time it takes your heart rate to recover after a high intensity workout, is a meaningful measure of total fitness. Embodiments leverage heart rate recovery and determine a standardized fitness score assessment that is based on an individual's heart rate recovery and age. This standard measure allows a person to track improvement in cardiac health by tracking her fitness score over time. Embodiments determine a fitness score that accounts for age and starting heart rate level so that the fitness score is comparable over long periods of time.

Figure 1:
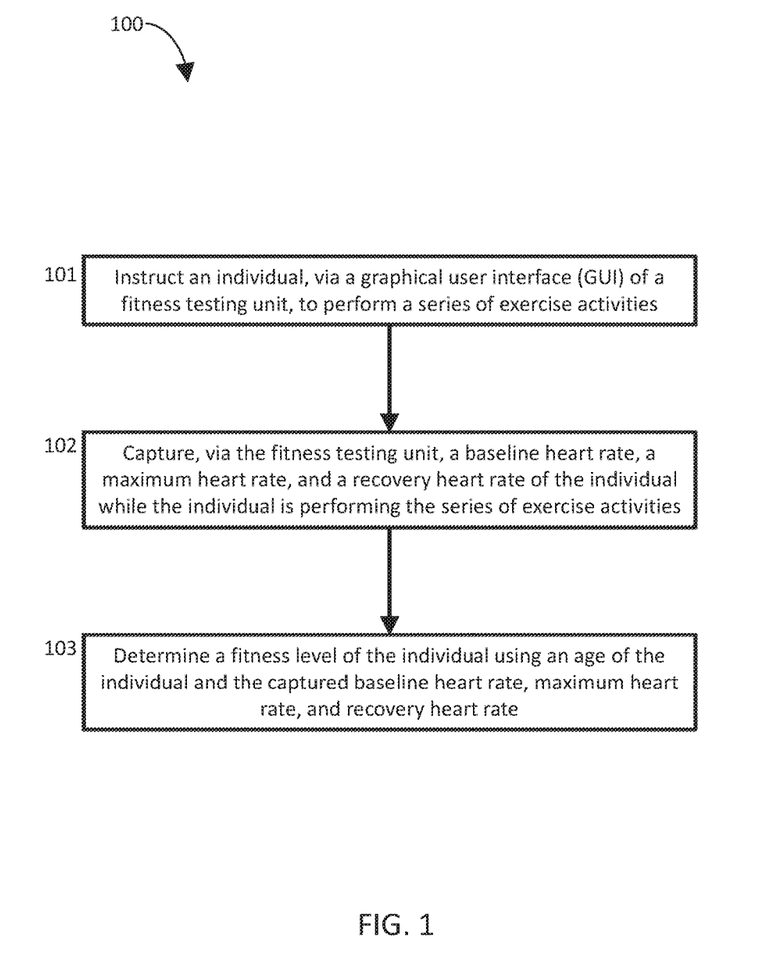
FIG. 1 is a flowchart of a method for determining the fitness level of an individual according to an embodiment.

FIG. 1 is a flowchart of method 100 for determining a fitness level of an individual using a fitness testing unit according to an embodiment. The method 100 begins at step 101 by instructing an individual, via a graphical user interface (GUI) of a fitness testing unit, to perform a series of exercise activities. According to an embodiment, the series of exercise activities includes exercises of increasing intensity with the goal of achieving a high percentage of maximum Heart rate to be used as the basis for HRR (Heart Rate recovery). The instructions in step 101 may be in any form that may be conveyed via the GUI. Further, an alternative embodiment of the method 100 may provide the instructions without the use of a GUI and may provide the instructions in any manner that can be perceived by an individual. Examples of such alternative methods for instructing the individual include mechanical instructions, e.g., vibration, and auditory instructions. Further, embodiments may use any combination of instruction modalities described herein.

In turn, at step 102, a baseline heart rate of the individual, a maximum heart rate of the individual, and a recovery heart rate of the individual are captured while the individual is performing the series of exercises the individual was instructed to perform in step 101. The heart rate of the individual may be captured at step 102 using any method of determining heart rate known in the art. For instance, in an embodiment, the individual wears a heart rate monitor that is communicatively coupled to the fitness testing unit and the heart rate monitor captures the individual's heart rate and communicates the individual's heart rate to the fitness testing unit via a communication protocol, e.g., Bluetooth.

To continue, at step 103, a fitness level of the individual is determined using an age of the individual and the captured baseline heart rate, maximum heart rate, and recovery heart rate. According to an embodiment, the fitness level of the individual is determined by calculating a fitness score that is a function of the individual's age and captured heart rate data. According to an embodiment, the fitness score ranges from 0 to 100. Further, in an embodiment, the fitness level is determined at step 103 using the following equation:

$$\text{Fitness Score} = \frac{(100 \times (\text{Max } HR - 1 \text{ Min Recovery } HR))}{((\text{Max } HR - \text{Baseline } HR) \times Z)}$$

where Baseline HR is the individual's base line heart rate measured while an individual is performing a relaxation activity, Max HR is the individual's maximum heart rate, 1 Min Recovery HR is the recovery heart rate measured after 1 minute of recovery, and Z is a heart rate recovery index based on age of the individual. Further details regarding calculating the fitness score and Z are described hereinbelow.

In an embodiment, the fitness level of the individual is determined by a processor associated with the fitness testing unit executing computer code instructions stored in memory. In an embodiment, the fitness level of the individual is determined by the fitness testing unit. In an alternative embodiment, the fitness level of the individual is determined by a computing device that is located remotely in relation to the individual. In such an alternative embodiment, the captured heart rate data is communicated to the remotely located computing device and the remotely located computing device determines the fitness level. According to an embodiment, the device computing the fitness level of the individual obtains the age of the individual. In an embodiment, the age is obtained via user input at the time of determining the individual's fitness level or by accessing stored age data associated with the user. Another embodiment obtains the age of the individual by accessing a database storing a user profile associated with the individual. In this way, at step 103, the age of the individual can be used in determining the fitness level of the individual. According to an embodiment, the age of the individual is used to select the Z value used to calculate the individual's fitness score. In another embodiment, gender and age of the individual are both used to select the Z value for calculating the fitness score.

In an embodiment of the method 100, the series of exercise activities the user is instructed to perform at step 101 includes: a relaxation activity, a cardiovascular activity, and a recovery activity. In such an embodiment, at step 102, the baseline heart rate is captured while the individual is performing the relaxation activity, the maximum heart rate is captured while the individual is performing the cardiovascular activity, and the recovery heart rate is captured while the individual is performing the recovery activity. Further, according to yet another embodiment of the method 100, instructing the individual to perform the series of activities at step 101 includes instructing the individual, via the GUI, to perform the cardiovascular activity until it is determined that the monitored heart rate of the individual is at 80% of a recommended heart rate. According to an embodiment, the recommended heart rate is based on the age of the individual. For instance, in one such example embodiment, maximum heart rate equals 220 minus age minus any adjustments which may be made for physical limitations.

In an embodiment of the method 100, capturing the individual's heart rate at step 102 includes continuously monitoring heart rate of the individual. Then, this continuously captured heart rate data is processed to identify the heart rate data needed, e.g., baseline heart rate, maximum heart rate, and recovery heart rate, to determine the individual's fitness level. According to yet another embodiment of the method 100, determining a fitness level of the individual using an age of the individual employs a factor indicating highest potential heart rate recovery given the age of the individual. Such a factor may be pre-determined based upon previous heart rate data captured for a plurality of individuals. This data may be stored in memory that is accessible to a computing device determining the fitness level so that the factor may be employed in determining the individual's fitness level.

Embodiments of the method 100 may be implemented using any computing device known in the art. For instance, the method 100 may be implemented on a computing device with instructions that cause a computer application to implement the method 100. Further, the fitness testing unit may be any such device capable of instructing an individual, via a GUI, to perform exercise activities, and capture heart rate of the individual. For example, the fitness testing unit may be implemented using a computing device including, memory, one or more processors, and one or more communication interfaces capable of performing the functionality described herein. Further, in another embodiment, the fitness testing unit comprises an exercise device on which the exercises the individual is instructed to perform at step 101 can be performed. Example exercise devices include a bicycle, a treadmill, and a rowing machine, amongst other examples.

Embodiments of the method 100 may perform a variety of functionalities using the fitness level, e.g., fitness score, determined at step 103. One such embodiment displays the fitness level to the individual in the GUI. In another embodiment, the fitness level determined at step 103 is stored. In yet another embodiment, the fitness level determined at step 103 is used to modify the user experience in future exercise activities. For instance, in an embodiment, the fitness level determined at step 103 is used to create a personalized workout for the user. This personalized workout may be automatically determined based upon the fitness level or the fitness level may be provided to a fitness instructor, i.e., trainer, who creates a workout for the user based upon the determined fitness level. According to yet another embodiment, the fitness level determined at step 103 is aggregated with determined fitness levels for a plurality of other individuals. In this way, such an embodiment may track fitness levels for a population or specific group.

The resulting fitness level determined at step 103 can also be tracked over time, which allows a user to assess his level of relative heart rate recovery and, therefore, track heart health over long periods of time. The fitness level, i.e., score, determined at step 103 allows for tracking fitness over a lifetime. Because the fitness level is determined at step 103 using the age of the individual, the fitness level measures relative health at any age. While heart rate recovery may change over time, the maximum fitness score, e.g., 100, is attainable at any age, since the factors used to determine this maximum score adjust with age.

The fitness level determined at step 103 can be used to automatically provide recommendations to users. For instance, the difficulty and intensity of workouts that users are instructed to perform can be automatically varied based on the user's fitness level. Likewise, fitness instructors can be recommended to a user based on the user's fitness level. In this way, a user can take a fitness class, e.g., view and remotely participate in a fitness class, that aligns with his or her fitness level. Further still, specific workouts and exercises can be recommended to a user based upon his fitness level in order to build the user's heart health. These aforementioned recommendations can all be done automatically, for example, through use of a database that stores instructor information, workout information, and recommended exercises and fitness levels that are appropriate for the various instructors, workouts, and exercises.

Figure 2:
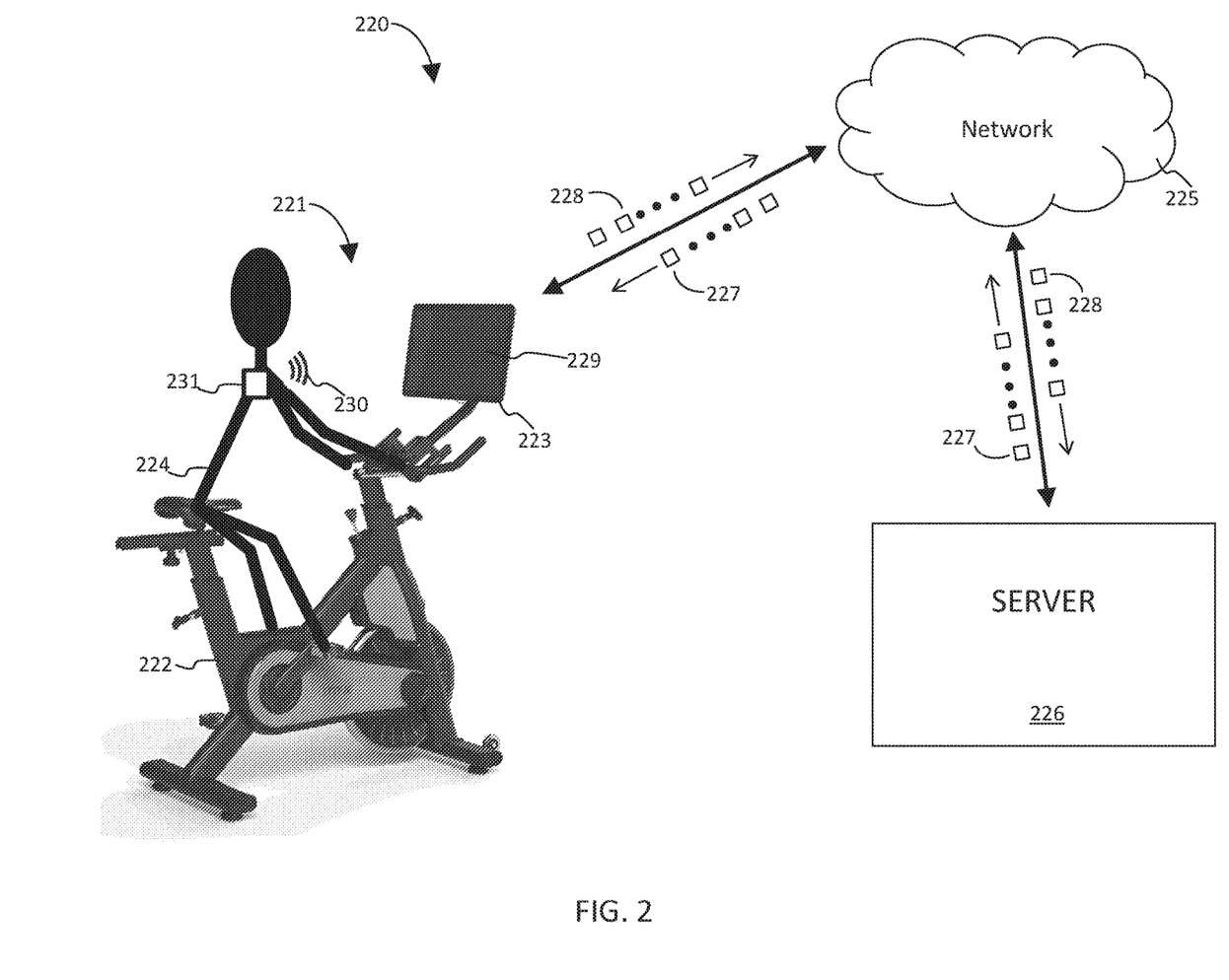
FIG. 2 is a diagram of an embodiment of a system for determining the fitness level of an individual.

FIG. 2 illustrates an environment 220 for determining the fitness level of an individual according to an embodiment. The environment 220 includes the fitness testing unit 221 that is configured to implement the embodiments described herein to determine a fitness level of the individual 224. The fitness testing unit 221 comprises the bicycle 222 and computing device 223. The environment 220 also includes the network 225 and server 226.

In an example implementation of the environment 220, instructions 227 to perform a series of exercises are sent from the server 226 via the network 225 to the computing device 223. The computing device 223 is configured to provide the instructions 227 in a graphical user interface on the display 229. The individual 224 follows the instructions 227 and performs the series of exercises. The individual 224 wears a heart rate monitor 231 (that may be any heart rate monitor known in the art) that captures the individual's 224 heart rate data while the individual 224 is performing the series of exercises from the instructions 227. The heart rate monitor 231 communicates the heart rate data via the communication 230 (which may be a Bluetooth communication) to the computing device 223 of the fitness testing unit 221. In an embodiment, the computing device 223 captures baseline heart rate, maximum heart rate, and recovery heart rate of the individual 224 while the individual 224 is performing the series of exercise activities. The computing device 223 determines a fitness level of the individual, e.g., computes a fitness score using the heart rate data obtained via the communication 230. Alternatively, the computing device 223 can send the heart rate data 228 via the network 225 to the server 226 and the server 226 or another associated computing device can determine the fitness level of the individual 224. Further, in an embodiment where the computing device 223 determines the individual's 224 fitness level, the computing device 223 may send the determined fitness level to the server 226. Moreover, in embodiments of the environment 220, the computing device 223 and/or server 226 may store the determined fitness level, e.g., fitness score of the individual. Further, in the environment 220, multiple fitness levels of the individual 224 may be determined over time and stored by the computing device 223 and/or server 226 so that the individual 224 may measure and track fitness progress over time.

Figure 3:
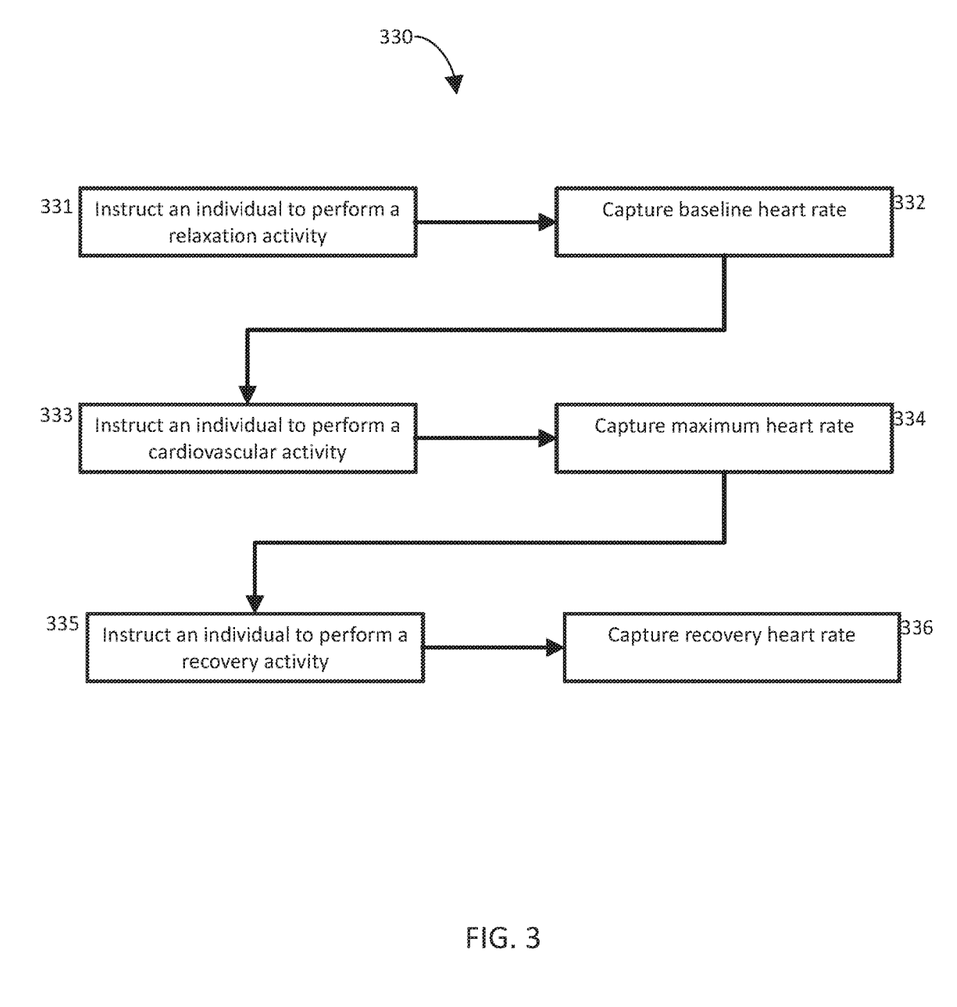
FIG. 3 is flowchart of a method for instructing an individual through a series of exercise activities and capturing heart rate of the individual while performing the activities according to an embodiment.

As part of determining a fitness level of an individual, embodiments determine a fitness score. In an embodiment, a standardized heart rate recovery workout, such as the workout the user is instructed to perform in the method 330 is used to determine an individual's fitness score. FIG. 3 illustrates an example method 330 for instructing an individual to perform a series of exercise activities and capture the individual's heart rate data while performing the activities. In the method 330, a participant is taken through a pre-set workout and the participant's heart rate is measured at pre-established times to determine baseline heart rate, maximum heart rate, and recovery heart rate.

The method 330 begins at step 331 by instructing an individual to perform a relaxation activity. While the individual is performing the relaxation activity, baseline heart rate is captured at step 332. At step 333, the individual is instructed to perform a cardiovascular activity and at step 334 the individual's heart rate while performing the cardiovascular activity is captured. To continue, at step 335 the individual is instructed to perform a recovery activity, such as deep breathing, and at step 336 recovery heart rate is measured.

According to an embodiment, at step 333, the individual is instructed to perform activities that increase the individual's heart rate to approximately 80% of the recommended maximum heart rate for the individual's age. In an embodiment, the maximum heart rate for any given age is calculated with the accepted industry standard:

Maximum Heart Rate=220–Age of Individual–any adjustments which may be made for physical limitations The cardiovascular activities the individual is instructed to perform at step 333 may be any such activities known in the art, e.g., running and/or cycling. Further, the instructions may be tailored and varied over time so that the user's heart rate reaches a desired level, e.g., 80% of recommended maximum heart rate.

In an embodiment of the method 330, baseline, maximum, and recovery heart rates may be captured at pre-determined times or, heart rate data may be captured and processed to determine baseline, maximum, and recovery heart rate. For example, heart rate data may be captured continuously while the individual is being instructed to, and is performing the relaxation activity. This continuously captured heart rate data may be processed to identify a minimum heart rate for the individual and the minimum heart rate would be the individual's baseline heart rate. Similar procedures may be employed for capturing maximum heart rate at step 334 and recovery heart rate at step 336. In an embodiment of the method 330, recovery heart rate may be captured at step 336 multiple times and at pre-determined times. For instance, in an example embodiment, the recovery heart rate is captured one minute and two minutes after starting to instruct the individual to perform the relaxation activity at step 335. Further, in another embodiment, the individual is instructed to perform the relaxation activity at step 335 upon reaching the maximum heart rate, e.g., 80% of recommended maximum heart rate, while performing the instructed cardiovascular activity. In such an embodiment, recovery heart rate may be captured at step 336 one minute and two minutes after the maximum heart rate (80% of recommended max) is reached.

The method 330 may be performed over a pre-determined period of time. For example, the user may be instructed at step 331 to perform 2 minutes of relaxation, e.g., mindfulness, being at rest, etc., activities. During these 2 minutes, heart rate data is captured 332 and the lowest point is taken as the baseline heart rate. Then, at step 333, the user is instructed to perform a cardiovascular activity for 15 to 25 minutes to ramp up heart rate and then, the highest heart rate captured 334 during that time period is the maximum heart rate. In turn, at step 335, the user is instructed to perform a recovery/cool down protocol, e.g., deep breathing, and heart rate is captured 336 after 1 minute of cooling down and after 2 minutes of cooling down.

As part of determining a fitness level of an individual, embodiments may determine a fitness score. In an embodiment, a fitness score is determined using the following equation, where the best possible score is 100 and the worst possible score is 0:

$$\text{Fitness Score} = \frac{(100 \times (\text{Max } HR - 1 \text{ Min Recovery } HR))}{((\text{Max } HR - \text{Baseline } HR) \times Z)}$$

where Baseline HR is the individual's base line heart rate measured while an individual is performing a relaxation activity, e.g., the heart rate measured at step 332 of the method 330, Max HR is the individual's maximum heart rate, e.g., the heart rate measured at step 334 of the method 330, 1 Min Recovery HR is the recovery heart rate measured after 1 minute of recovery, e.g., the heart rate measured at step 336 of the method 330, and Z is a heart rate recovery index based on the age of the individual. It is noted that while the above equation utilizes 1 Min Recovery HR (the recovery heart rate measured after 1 minute of recovery), embodiments are not so limited and may use a recovery heart rate measured at various points in time, e.g., 1 minute, 2 minutes, 5 minutes etc. In an embodiment, the heart rate recovery data used is based on past measurements, i.e., if 1 minute heart rate recovery was used in the past, 1 minute heart rate recovery is used again so that a user can track his fitness level over time. Further, in an embodiment, the heart rate recovery data used is selected to correspond to the Z (heart rate recovery index) that is used in calculating the fitness score. As described hereinbelow, Z is based on fitness level scores from a plurality of individuals. If Z is calculated using 2 minute heart rate recovery data for the plurality of individuals, then, 2 minute heart rate recovery data is used when using said Z score. Similarly, if Z is calculated using 1 minute heart rate recovery data, then, 1 minute heart rate recovery data is used when using said Z score to calculate a fitness score. In this way, in such an embodiment, the heart rate recovery data and Z are chosen to correspond and, Z is also selected to correspond with the individual's age. Further, in embodiments, Z may also be chosen to correspond with the individual's gender. In other words, Z may be calculated for particular genders, e.g., there is a Z value for 30 year old females and a different Z value for 30 year old males. In an embodiment, Z represents the highest potential recovery of heartrate after 2 minutes for people of that age. According to an embodiment, Z indicates the best possible fitness level an individual may attain at her age. In this way, embodiments account for age when determining fitness level. In embodiments, Z is a number derived from actual heart rate recovery data from a plurality of individuals and Z represents the maximum potential percentage recovery from a maximum heart rate to the baseline heart rate for someone of a certain age. Further, Z may also be specific to gender. In other words, in such an embodiment, Z represents the maximum potential percentage recovery from a maximum heart rate to the baseline heart rate for someone of a certain age and gender. Further details and examples for determining Z are described hereinbelow.

To illustrate calculating a fitness score, consider the example, where baseline heart rate is 75 beats per minute (BPM), 80% maximum heart rate is 180 BPM, recovery heart rate after 1 minute is 152 BPM, recovery heart rate is 125 BPM after 2 minutes, and Z (based on the user's age of 45) is 45%. Given these values, the individual's fitness score is:

$$\text{Example 1: Fitness Score} = 59.3 = \frac{(100 \times (180 - 152))}{((180 - 75) \times .45)}$$

Another example participant has a low fitness level. In this example, baseline heart rate is 75 beats per minute (BPM), 80% maximum heart rate is 180 BPM, recovery heart rate after 1 minute is 173 BPM, recovery heart rate is 164 BPM after 2 minutes, and Z (based on the user's age of 45) is 45%. Given these values, the individual's fitness score is:

$$\text{Example 2: Fitness Score} = 14.8 = \frac{(100 \times (180 - 173))}{((180 - 75) \times .45)}$$

In another example, the user is 65 years old, baseline heart rate is 75 beats per minute (BPM), 80% maximum heart rate is 160 BPM, recovery heart rate after 1 minute is 132 BPM, recovery heart rate is 105 BPM after 2 minutes, and Z (based on the user's age of 65) is 48%. Given these values, the individual's fitness score is:

$$\text{Example 3: Fitness Score} = 68.6 = \frac{(100 \times (160 - 132))}{((160 - 75) \times .48)}$$

In yet another example, the user is 65 years old, baseline heart rate is 75 beats per minute (BPM), 80% maximum heart rate is 160 BPM, recovery heart rate after 1 minute is 154 BPM, recovery heart rate is 145 BPM after 2 minutes, and Z (based on the user's age of 65) is 48%. Given these values, the individual's fitness score is:

$$\text{Example 4: Fitness Score} = 14.7 = \frac{(100 \times (160 - 154))}{((160 - 75) \times .48)}$$

The above examples illustrate the power of the determined fitness score and how the fitness score varies with age. The users in Example 1 and Example 3 have the same heart rate recovery, 28 beats per minute in 1 minute, however, the user in Example 1 is less fit (fitness score 59.3) than the user in Example 3 (fitness score 68.6) because the user in Example 1 is younger and should have a greater drop in heart rate from his max. The users in Examples 2 and 4 have similar fitness scores, but the user in Example 4 has a much lower max heart rate and a slower hear rate recovery (as expected for his age) and, thus, the users in Examples 2 and 4 have comparable fitness levels despite their differing scores for max heart rate and recovery heart rate.

In an embodiment, fitness scores can be used to track fitness level over time. When someone first starts on a fitness plan, his heart rate recovers more slowly after exertion. Initially, a person's heart rate may drop only 10-15 BPM after 1 minute, or 20-25 BPM after 2 minutes. As the person progresses and becomes more fit, he can expect a heart rate drop of 20-30 BPM after 1 minute and 40-60 BPM or more after 2 minutes depending on age. These improvements can be measured and tracked overtime by repeating the methods described herein.

According to an embodiment, Z is based on historical heart rate data collected from a plurality of individuals. For example, in embodiments, the historical heart rate data may be collected from a plurality of individuals while performing methods described herein, e.g., the method 100 or the historical heart data may be existing data, such as data from a medical study, amongst other examples. In an embodiment, Z is calculated using the following equation:

$$Z = \frac{(\text{Average } HRR + (3 \times STD))}{(\text{Average Peak } HR - \text{Average Resting } HR)}$$

where Average HRR is the average heart rate recovery amongst individuals of a particular age or age cohort, STD is the standard deviation of the heart rate recovery data of the individuals, Average Peak HR is the average peak heart rate measured while individuals of the particular age (or age cohort) are performing cardiovascular activity, and Average Resting HR is the average resting heart rate of individuals of that particular age (or age cohort). According to embodiment, Z is calculated for various age cohorts, e.g., 30 to 39 years old, 40 to 49 years old, 50 to 59 years old, etc. In an alternative embodiment, a Z value is calculated for each individual age, e.g., there is a Z for age 40, a Z for age 41, etc. In embodiments, Z may also be calculated for particular genders as well as ages. In such embodiments, the same calculation of Z as described above is used however, the heart rate recovery data used for calculating Z is all collected from male or female participants depending on whether a male Z value or female Z value is being calculated. When calculating a fitness score as described herein, a Z value is selected that corresponds to the age and/or gender and/or time period of recovery of the individual for which the fitness score is being calculated.

Further, it is noted that embodiments may modify the Z value calculation so as to modify the range of possible fitness scores. For instance, the above equation calculates a Z score that is based upon three standard deviations (the equation component 3×STD), however, embodiments may calculate a Z value based upon a different number of standard deviations. For example, Z may be calculated based upon two standard deviations. In such an example, Z is given by the following equation:

$$Z = \frac{(\text{Average } HRR + (2 \times STD))}{(\text{Average Peak } HR - \text{Average Resting } HR)}$$

To illustrate calculating Z, consider the example where heart rate data was collected for 1000 people between the ages of 30 to 39, and from this data, the average heart rate recovery 1 minute after stopping the cardiovascular exercise is 22.9, the standard deviation of the heart rate recovery data 1 minute after stopping the cardiovascular exercise is 8.34, the average peak heart rate is 182.4, and the average resting heart rate is 76.1. Given these values, Z for the 30 to 39 cohort is:

$$Z = 45.1\% = \frac{(22.9 + (3 \times 8.34))}{(182.4 - 76.1)}$$

Figure 4:
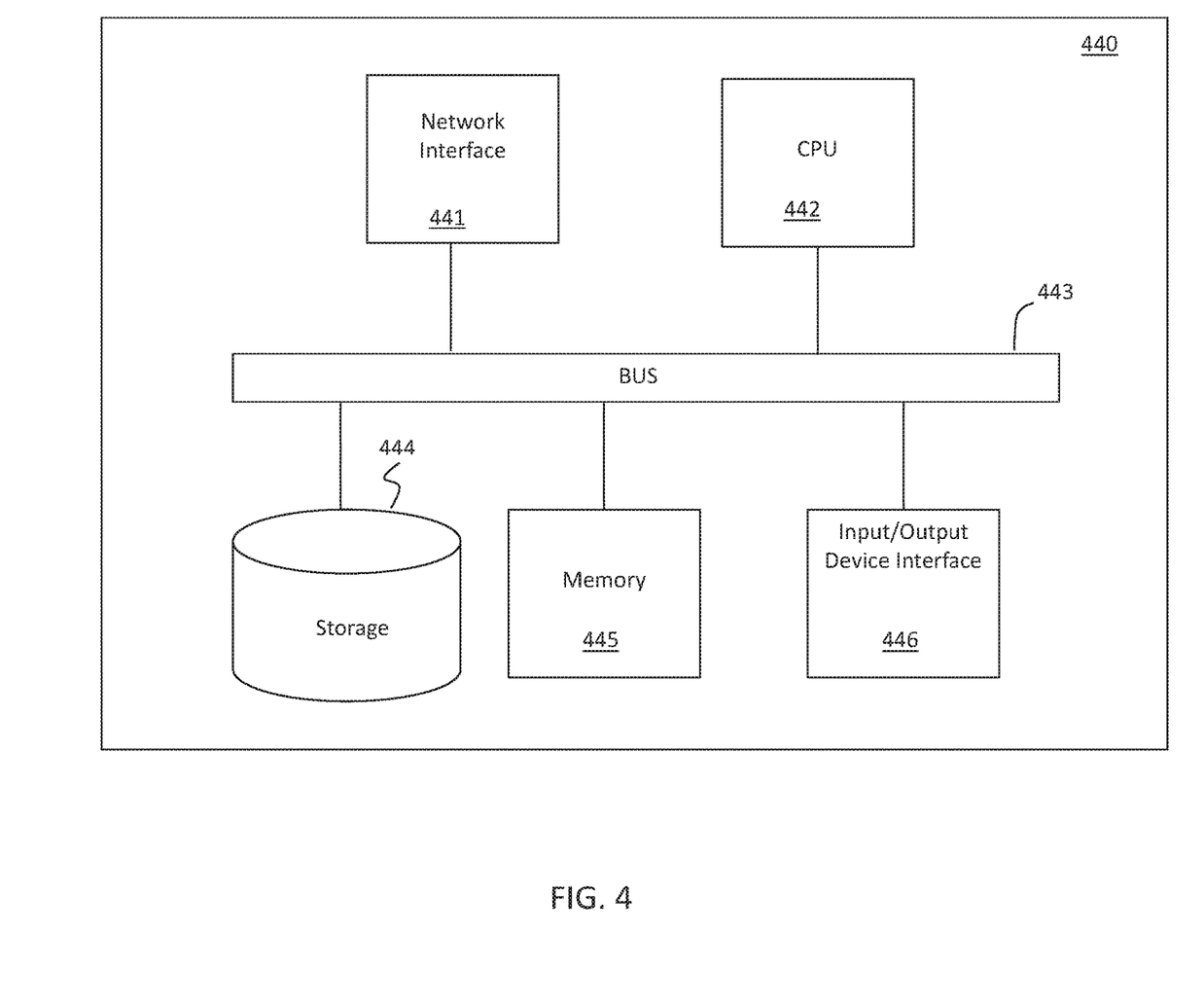
FIG. 4 is a simplified block diagram of a computing system for determining fitness level of an individual according to an embodiment.

FIG. 4 is a simplified block diagram of a computer-based system 440 that may be used to determine fitness level of an individual according to any variety of the embodiments of the present invention described herein. The system 440 comprises a bus 443. The bus 443 serves as an interconnect between the various components of the system 440. Connected to the bus 443 is an input/output device interface 446 for connecting various input and output devices such as a keyboard, mouse, display, speakers, etc. to the system 440. A central processing unit (CPU) 442 is connected to the bus 443 and provides for the execution of computer instructions. Memory 445 provides volatile storage for data used for carrying out computer instructions. Storage 444 provides non-volatile storage for software instructions, such as an operating system (not shown). The system 440 also comprises a network interface 441 for connecting to any variety of networks known in the art, including wide area networks (WANs) and local area networks (LANs).

It should be understood that the example embodiments described herein may be implemented in many different ways. In some instances, the various methods and machines described herein may each be implemented by a physical, virtual, or hybrid general purpose computer, such as the computer system 440, or a computer network environment such as the computer environment 550, described herein below in relation to FIG. 5. The computer system 440 may be transformed into the machines that execute the methods described herein, for example, by loading software instructions into either memory 445 or non-volatile storage 444 for execution by the CPU 442. One of ordinary skill in the art should further understand that the system 440 and its various components may be configured to carry out any embodiments or combination of embodiments of the present invention described herein. Further, the system 440 may implement the various embodiments described herein utilizing any combination of hardware, software, and firmware modules operatively coupled, internally, or externally, to the system 440.

Figure 5:
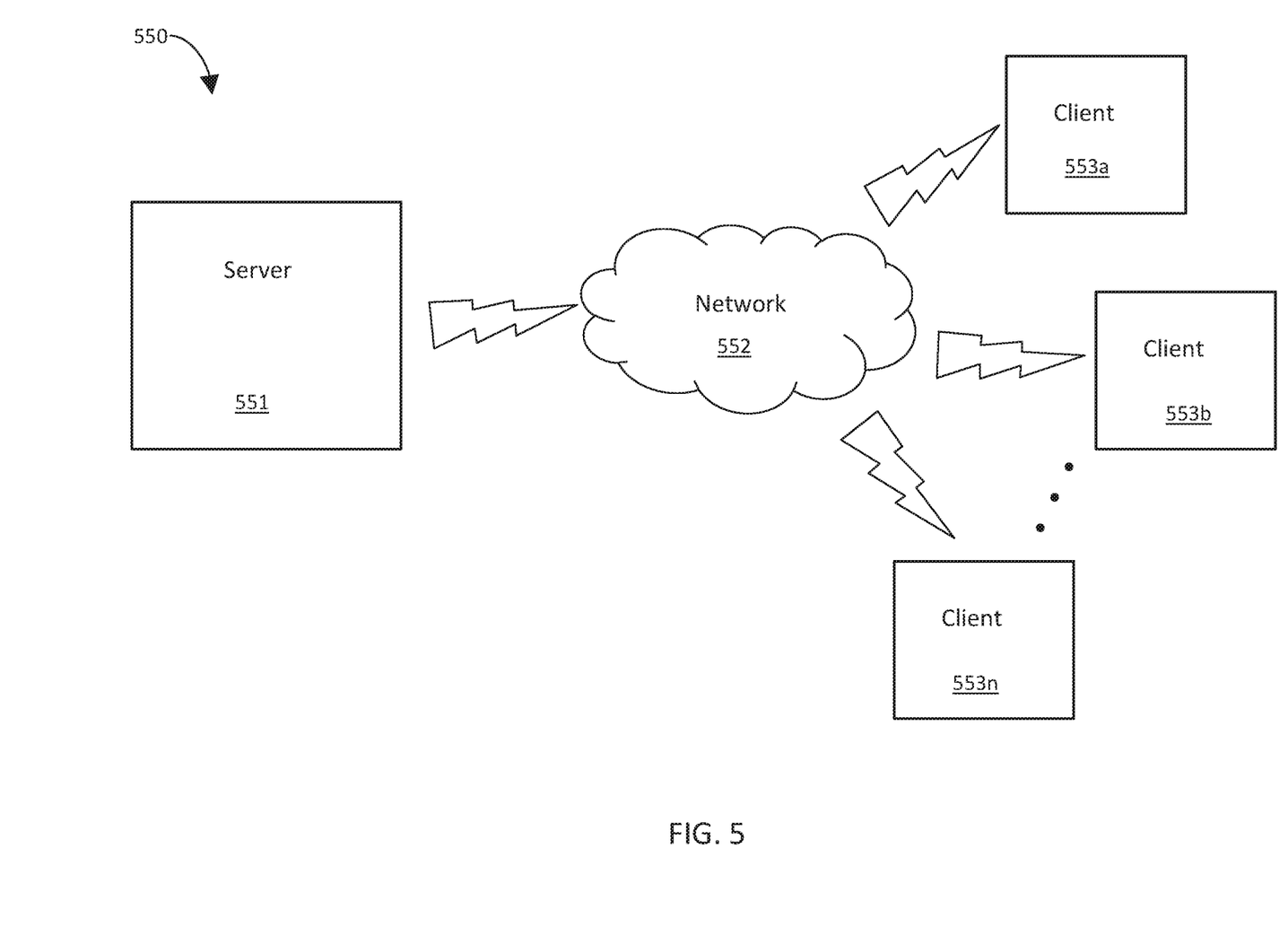
FIG. 5 is a simplified diagram of a computer network environment in which an embodiment of the present invention may be implemented.

FIG. 5 illustrates a computer network environment 550 in which an embodiment of the present invention may be implemented. In the computer network environment 550, the server 551 is linked through the communications network 552 to the clients 553*a-n*. The environment 550 may be used to allow the clients 553*a-n*, alone or in combination with the server 551, to execute any of the methods described herein.

Embodiments or aspects thereof may be implemented in the form of hardware, firmware, or software. If implemented in software, the software may be stored on any non-transient computer readable medium that is configured to enable a processor to load the software or subsets of instructions thereof. The processor then executes the instructions and is configured to operate or cause an apparatus to operate in a manner as described herein.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and thus, the data processors described herein are intended for purposes of illustration only and not as a limitation of the embodiments.

While example embodiments have been particularly shown and described, it will be understood by those skilled in the art that various changes in form and details may be made therein without departing from the scope of the embodiments encompassed by the appended claims.

What is claimed is:

1. A method for determining a fitness level of an individual using a fitness testing unit, the method comprising:
   instructing an individual, via a graphical user interface (GUI) of a fitness testing unit, to perform a series of exercise activities;
   capturing, via the fitness testing unit, a baseline heart rate, a maximum heart rate, and a recovery heart rate of the individual while the individual is performing the series of exercise activities; and
   determining a fitness level of the individual using an age of the individual and the captured baseline heart rate, maximum heart rate, and recovery heart rate,
   wherein determining the fitness level of the individual using the age of the individual employs a factor indicating highest potential heart rate recovery given the age of the individual.

2. The method of claim 1 wherein the series of exercise activities includes exercises of varying intensity.

3. The method of claim 2 wherein the series of exercise activities includes: a relaxation activity, a cardiovascular activity, and a recovery activity.

4. The method of claim 3 wherein the baseline heart rate is captured while the individual is performing the relaxation activity, the maximum heart rate is captured while the individual is performing the cardiovascular activity, and the recovery heart rate is captured while the individual is performing the recovery activity.

5. The method of claim 3 wherein capturing includes continuously monitoring heart rate of the individual and instructing the individual to perform the series of activities includes:
   instructing the individual, via the GUI, to perform the cardiovascular activity until it is determined that the monitored heart rate is at 80% of a recommended heart rate, wherein the recommended heart rate is based on the age of the individual.

6. The method of claim 1 further comprising:
   obtaining the age of the individual by accessing a database storing a user profile associated with the individual.

7. The method of claim 1 wherein the fitness testing unit comprises a bicycle or a treadmill.

8. The method of claim 1 further comprising, at least one of:
   storing the determined fitness level;
   displaying the determined fitness level in the GUI;
   aggregating the determined fitness level of the individual with fitness level data for multiple individuals; and
   providing exercise instructions to the individual based upon the determined fitness level.

9. A fitness testing system for determining a fitness level of an individual, the system comprising:
   a processor and a memory with computer code instructions stored thereon, the processor and the memory, with the computer code instructions, being configured to cause the fitness testing system to:
   instruct an individual, via a graphical user interface (GUI) of the fitness testing system, to perform a series of exercise activities; capture a baseline heart rate, a maximum heart rate, and a recovery heart rate of the individual while the individual is performing the series of exercise activities; and determine a fitness level of the individual using an age of the individual and the captured baseline heart rate, maximum heart rate, and recovery heart rate, wherein determining the fitness level of the individual using the age of the individual employs a factor indicating highest potential heart rate recovery given the age of the individual.

10. The system of claim 9 wherein the series of exercise activities includes exercises of varying intensity.

11. The system of claim 10 wherein the series of exercise activities includes: a relaxation activity, a cardiovascular activity, and a recovery activity.

12. The system of claim 11 where, in capturing the baseline heart rate, the maximum heart rate, and the recovery heart rate, the processor and the memory, with the computer code instructions, are configured to cause the fitness testing system to:

capture the baseline heart rate while the individual is performing the relaxation activity;

capture the maximum heart rate while the individual is performing the cardiovascular activity; and capture the recovery heart rate while the individual is performing the recovery activity.

13. The system of claim 11 where, in the capturing and instructing, the processor and the memory, with the computer code instructions, are further configured to cause the fitness testing system to:

continuously monitor heart rate of the individual; and instruct the individual, via the GUI, to perform the cardiovascular activity until it is determined that the monitored heart rate is at 80% of a recommended heart rate, wherein the recommended heart rate is based on the age of the individual.

14. The system of claim 9 wherein the processor and the memory, with the computer code instructions, are further configured to cause the fitness testing system to:

obtain the age of the individual by accessing a database storing a user profile associated with the individual.

15. The system of claim 9 wherein the fitness testing system is integrated into a bicycle or treadmill.

16. The system of claim 9 wherein the processor and the memory, with the computer code instructions, are further configured to cause the fitness testing system to perform at least one of:

storing the determined fitness level;

displaying the determined fitness level in the GUI;

aggregating the determined fitness level of the individual with fitness level data for multiple individuals; and providing exercise instructions to the individual based upon the determined fitness level.

17. A computer program product for determining a fitness level of an individual using a fitness testing unit, the computer program product comprising:

one or more non-transitory computer-readable storage devices and program instructions stored on at least one of the one or more storage devices, the program instructions, when loaded and executed by a processor associated with the fitness testing unit, cause the fitness testing unit to:

instruct an individual, via a graphical user interface (GUI) of the fitness testing unit, to perform a series of exercise activities;

capture a baseline heart rate, a maximum heart rate, and a recovery heart rate of the individual while the individual is performing the series of exercise activities; and determine a fitness level of the individual using an age of the individual and the captured baseline heart rate, maximum heart rate, and recovery heart rate, wherein determining the fitness level of the individual using the age of the individual employs a factor indicating highest potential heart rate recovery given the age of the individual.

18. The computer program product of claim 17 wherein the series of exercise activities includes: a relaxation activity, a cardiovascular activity, and a recovery activity.

19. The method of claim 18 where, in capturing the baseline heart rate, the maximum heart rate, and the recovery heart rate, the program instructions cause the fitness testing unit to:

capture the baseline heart rate while the individual is performing the relaxation activity;

capture the maximum heart rate while the individual is performing the cardiovascular activity; and capture the recovery heart rate while the individual is performing the recovery activity.

20. The computer program product of claim 17 wherein, the program instructions cause the fitness testing unit to perform at least one of:

storing the determined fitness level;

displaying the determined fitness level in the GUI;

aggregating the determined fitness level of the individual with fitness level data for multiple individuals; and providing exercise instructions to the individual based upon the determined fitness level.

* * * * *